United States Patent
Bennett et al.

(10) Patent No.: US 7,139,071 B2
(45) Date of Patent: Nov. 21, 2006

(54) SPECTROSCOPY APPARATUS AND METHOD

(75) Inventors: Robert Bennett, Nympsfield (GB); John Charles Clifford Day, Bristol (GB); Graham Mark Meaden, Bristol (GB)

(73) Assignee: Renishaw PLC, Gloucestershire (GB)

( * ) Notice: Subject to any disclaimer, the term of this patent is extended or adjusted under 35 U.S.C. 154(b) by 366 days.

(21) Appl. No.: 10/471,415

(22) PCT Filed: Mar. 14, 2002

(86) PCT No.: PCT/GB02/01038

§ 371 (c)(1),
(2), (4) Date: Sep. 11, 2003

(87) PCT Pub. No.: WO02/075292

PCT Pub. Date: Sep. 26, 2002

(65) Prior Publication Data

US 2004/0090621 A1    May 13, 2004

(30) Foreign Application Priority Data

Mar. 15, 2001 (GB) ................................. 0106342.9

(51) Int. Cl.
G01J 3/44 (2006.01)
(52) U.S. Cl. ..................................................... 356/300
(58) Field of Classification Search ................ 356/300; 250/311
See application file for complete search history.

(56) References Cited

U.S. PATENT DOCUMENTS

| 4,407,008 | A | | 9/1983 | Schmidt et al. |
|---|---|---|---|---|
| 5,510,894 | A | | 4/1996 | Batchelder et al. |
| 6,002,476 | A | * | 12/1999 | Treado ........................ 356/301 |
| 6,095,982 | A | * | 8/2000 | Richards-Kortum et al. .......................... 356/301 |
| 6,281,657 | B1 | | 8/2001 | Matsuo |

FOREIGN PATENT DOCUMENTS

| DE | 100 14 636 A 1 | 10/2000 |
|---|---|---|
| EP | 0 542 962 B2 | 5/1993 |
| EP | 543 578 B1 | 5/1993 |
| JP | 11-133306 | 5/1999 |
| WO | WO 99/58939 | 11/1999 |
| WO | WO 01/94897 A1 | 12/2001 |

* cited by examiner

Primary Examiner—Hwa (Andrew) Lee
Assistant Examiner—Kara Geisel
(74) Attorney, Agent, or Firm—Oliff & Berridge, PLC

(57) ABSTRACT

A spectroscopy method in which a sample is scanned without moving the sample. Light from the sample 16 is collected by a lens 14 and analyzed at a spectrum analyzer 28 before being focused onto a photodetector 32. Light from the focal point of the lens 14 is brought to a tight focus on the photodetector 32 whilst light from in front of or behind the focal point comes to a more diffuse focus. Light from the pixels on the photodetector 32 corresponding to the focal point of the lens 14 is processed, whilst light from pixels outside this region is ignored, thus forming a 'virtual slit'. The sample 16 is scanned in a vertical direction by moving the 'virtual slit' up and down, by changing the designated rows of pixels from which data is analyzed. The sample is scanned in a horizontal direction by moving a vertical slit 24 in the light path in a horizontal direction.

26 Claims, 6 Drawing Sheets

SPECTROSCOPY APPARATUS AND METHOD

This invention relates to apparatus and methods in which spectroscopy is used to analyse a sample and in which the sample may be scanned to create a two or three-dimensional map.

In our earlier European Patent Application No. 0543578, a sample is irradiated with monochromatic light from a laser, and the scattered light is analysed in order to select a particular line of the resulting Raman spectrum. The analysis may be performed by a dispersive device such as a diffraction grating or it may be performed using a non-dispersive tunable filter. The resulting Raman scattered light may be focused onto a charge-coupled device (CCD), which is a two-dimensional photodetector array.

European Patent Application No. 0542962 discloses a method of spectroscopy as above in which one-dimensional confocality is achieved by use of a spatial filter (i.e. a confocal slit) in the optical path between the sample and the analyser. A second dimension of confocality is created by a process in which only the light received within a given area on the photodetector corresponding to light scattered from a given focal plane on the sample is analysed whilst light received from outside this given area on the photodetector corresponding to light scattered from outside the given focal plane on the sample is ignored. In this method, it is necessary to move the sample in an X-Y raster scan, if it is desired to produce a map of the sample.

Other spectroscopic techniques are known in which an electron microscope is combined with a spectroscopy system, for example Raman, photoluminescence or cathodoluminescence spectroscopy e.g. as described in International Patent Application No. WO99/58939. The present invention is also applicable to such techniques.

A first aspect of the present invention provides a spectroscopy method comprising: illuminating or irradiating a sample to obtain a spectrum of scattered light; analysing the spectrum; passing at least one component of the analysed spectrum to a photodetector, wherein light scattered from a given plane in the sample is brought to a tight focus in a given area on the photodetector and light scattered from other planes in the sample is brought to a more diffuse focus on the photodetector; wherein light received in said given area is detected without or separately from light outside the given area, thereby reducing the effect of light scattered from other planes in the sample; characterised in that the position of the given area on the photodetector in which light received is detected may be moved in order that light from a first point in a given plane of the sample is detected by the given area in a first position on the photodetector and light from a second point in the given plane in the sample is detected by the given area in a second position on the photodetector.

Preferably the step of detecting light in said given area on the photodetector provides confocal action in one dimension. To this end, the given area may be elongate.

Preferably confocal action is provided in a second dimension by providing a spatial filter through which the scattered light passes, comprising a screen with a slit positioned such that light from a given plane in the sample passes through the slit but light from other planes in the sample are blocked by the screen.

Preferably the slit is movable such that in a first position, light from only a first point on the sample may pass through the slit onto the photodetector, and in a second position light from only a second point in the sample may pass through the slit onto the photodetector.

The photodetector may comprise a two-dimensional array of photodetector elements. The wavenumber versus position on the array in a direction transverse to the slit may be calibrated for the initial position of the slit and a calibration correction performed for each subsequent position of the slit.

The spectroscopy apparatus may be positioned remotely from the sample by providing at least one optical fibre between the sample and the spatial filter for passage of scattered light from the sample to the spatial filter.

A second aspect of the present invention provides a spectroscopy method comprising: illuminating or irradiating a sample to obtain a spectrum of scattered light; analysing the spectrum; passing at least one component of the analysed spectrum to a photodetector; wherein the scattered light is passed through a confocal aperture to reduce light from non-desired planes which is passed to the photodetector; and wherein the aperture is movable such that in a first position, light from a first point in the sample may pass through the aperture onto the photodetector, and in a second position light from a second point in the sample may pass through the aperture onto the photodetector.

In this second aspect, the confocal aperture may be a slit, as in the first aspect. The wavenumber versus position on the photodetector may also be calibrated as in the first aspect.

Preferred embodiments of the invention will now be described by way of example, with reference to the accompanying drawings, wherein.

The first embodiment of the apparatus shown is based on the apparatus disclosed in EP 0542962.

Figure 1:
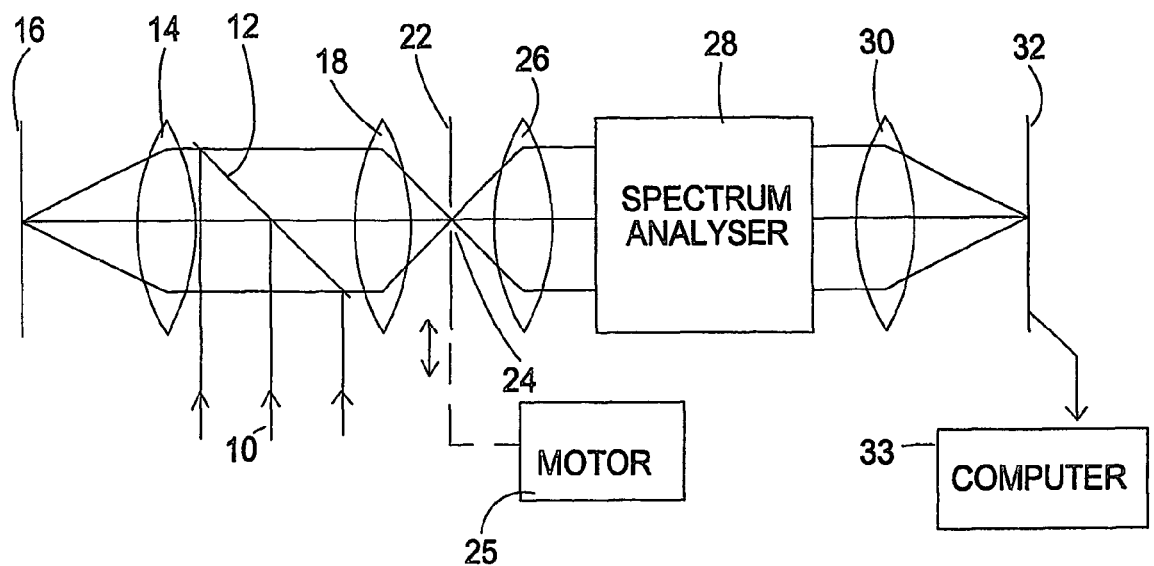
FIG. 1 is a schematic diagram of a first embodiment of Raman analysis apparatus.

As shown in FIG. 1, an input laser beam 10 is reflected through 90° by a dichroic filter 12 placed at 45° to the optical path and then focused by an objective lens 14 onto a point on the sample 16. The dichroic filter may alternatively be at a low angle of incidence as explained in EP 0543578. Alternatively, a notch filter may be used. Light scattered from this point on the sample is collected by the objective lens 14, collimated into a parallel beam and passed to the dichroic filter 12. The dichroic filter rejects the Rayleigh scattered light having the same frequency as the input beam but transmits the Raman scattered light. The Raman scattered light is brought to a tight focus by a lens 18 at a spatial filter comprising a screen 22 with a slit 24. Light scattered from the focal point of the objective lens passes through the slit 24. Most of the light scattered from behind or in front of the focal point is blocked by the screen 22 as it does not come to a focus at the slit 24. Thus the slit confers one-dimensional confocality to the scattered light. Light passing through the slit 24 is collimated by a lens 26 to a parallel beam and passed through a (spectrum) analyser 28. The analyser may produce a spectrum (i.e. when a grating is used) or select light from just one frequency (e.g. by using a tunable non-dispersive filter). A lens 30 brings the analysed light to a tight focus on the photodetector, which may be a charge-coupled device (CCD) 32.

Figure 2:
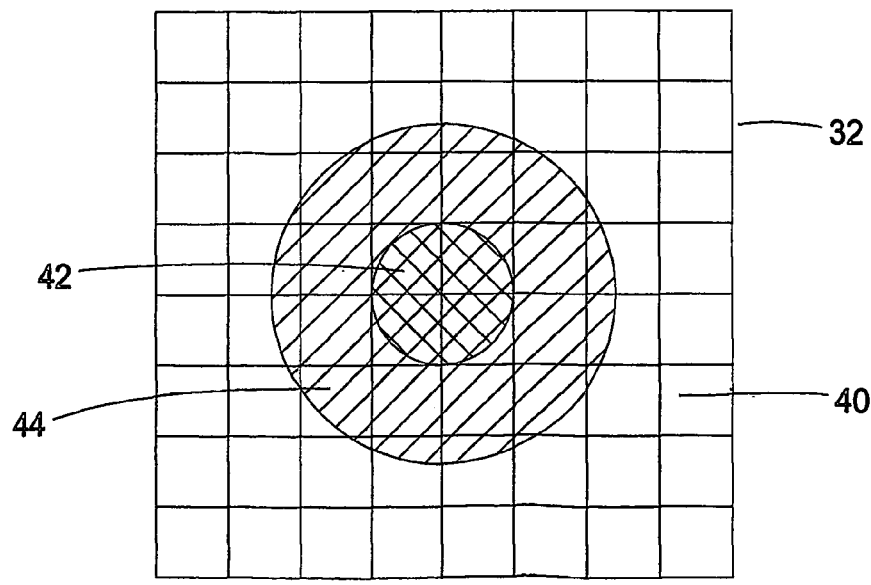
FIG. 2 is a schematic plan view of a charge-coupled device used in FIG. 1.

The CCD 32 comprises a two-dimensional array of pixels 40 (shown in FIG. 2) which is connected to a computer 33 to acquire and analyse data from each of the pixels. In the case where the (spectrum) analyser 28 comprises a tunable non-dispersive filter, light of the selected Raman frequency is focused on the CCD 32. Light from the focal point of the lens 14 is brought to a tight focus on the CCD at 42, however light from in front of or behind the focal point comes to a more diffuse focus at 44.

Figure 3:
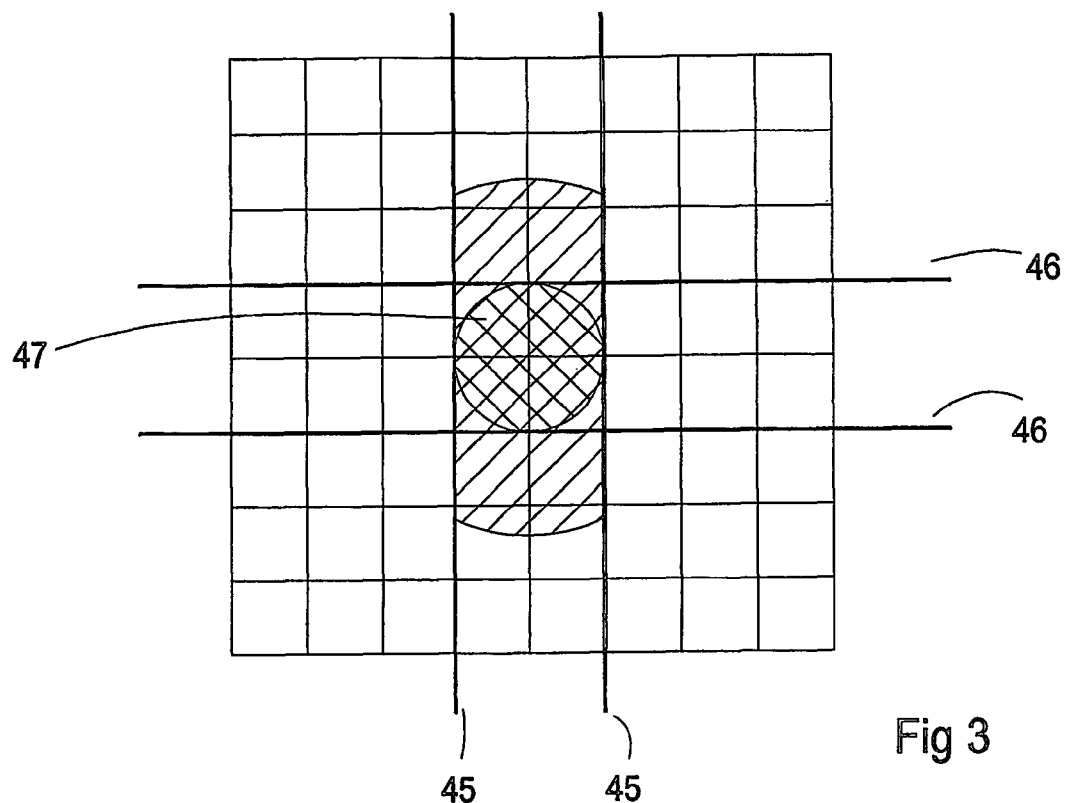
FIG. 3 is a schematic plan view of the charge-coupled device of FIG. 2 with use of a spatial filter and a virtual slit;.

The spatial filter provides one-dimensional confocality in the horizontal direction as seen in FIG. 3, resulting in light incident on the CCD 32 falling only between lines 45. However some light from outside the focal point can still be passed through the slit and received on the CCD. As shown in FIG. 3, to overcome this data from the pixels 40 between lines 46 which receive light from the focal point 19 is binned together vertically and extraneous light from outside the lines 46 is ignored. This binning together of the pixels may be done either at the computer 33 or the CCD chip 32. This analysis gives one-dimensional confocality in the vertical direction and acts as a "virtual slit". The result of the spatial filter and virtual slit is a group of pixels 47 on the CCD corresponding to a point on the sample.

Figure 4:
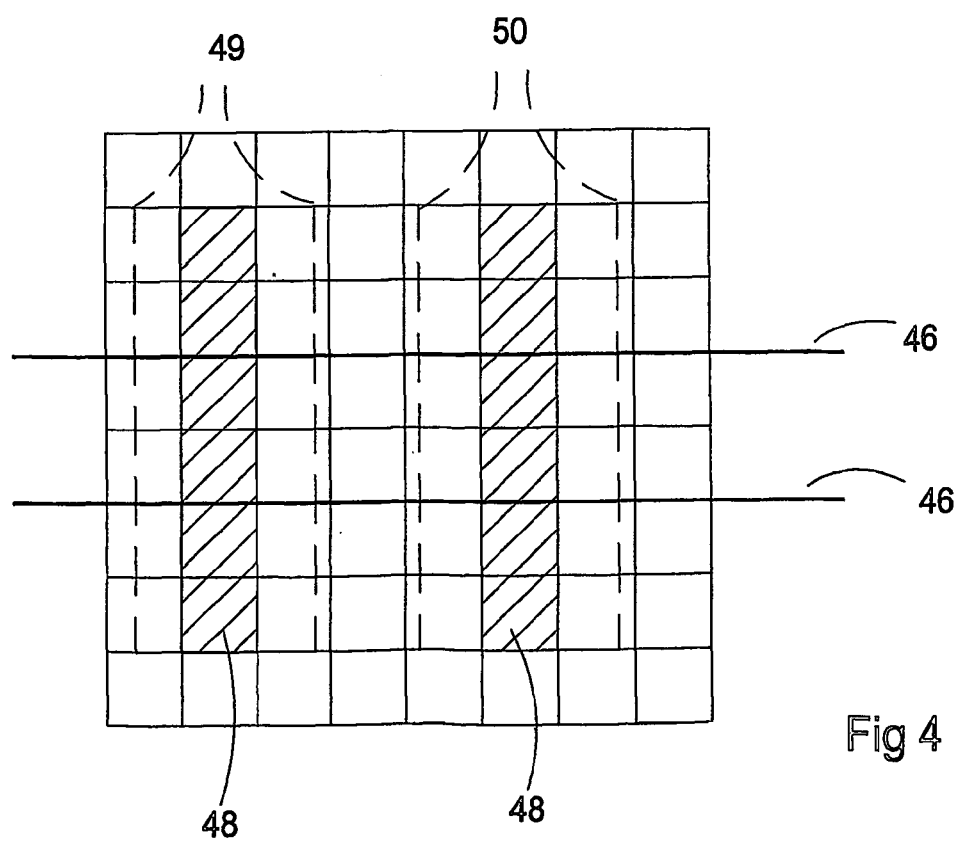
FIG. 4 is a schematic plan view of the charge-coupled device with use of a dispersive device.

In the case where a diffraction grating or other dispersive device is used as the analyser 28, a Raman spectrum is dispersed across the CCD 32 in a line as shown in FIG. 4. To obtain one-dimensional confocal behaviour, the computer or CCD chip is programmed to capture data from only those pixels of the CCD lying in the region between the lines 46 thus forming a virtual slit. As above, this data is binned vertically. Light from elsewhere in the CCD corresponding to light outside the focal plane on the sample is excluded.

The use of a spatial filter adds a second dimension of confocality. Without the slit, light corresponding to bands 48 scattered from outside the focal point 19 would appear in broader regions lying between the pairs of broken lines 49, 50.

Using this technique, it is possible to build up a two-dimensional map of the sample. This may be done without moving the sample, as follows.

To scan the sample, the laser is defocused on the sample, so that all, or at least part of, the sample is illuminated.

The sample is scanned in a vertical direction by moving the "virtual slit" up and down. This is achieved by the computer changing the designated row(s) of pixels which it bins together and analyses. As each row of pixels on the CCD receives light scattered from a corresponding row on the sample, by moving the "virtual slit" one row at a time a one-dimensional map may be made of the sample, without the sample having been moved.

Figure 5:
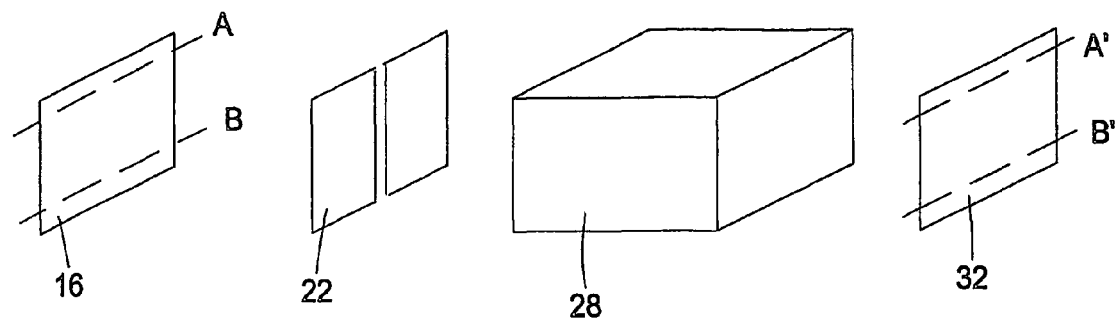
FIG. 5 is a schematic view of the first embodiment showing a virtual slit.

Thus as shown in FIG. 5, when the "virtual slit" is in position A', light scattered from row A in the sample is analysed. When the "virtual slit" is in position B', light scattered from row B in the sample is analysed.

Each row of the sample may also be scanned in the horizontal direction. This is achieved by the position of the slit being able to move horizontally, perpendicular to the optical path. This may be achieved by a motor 25 in FIG. 1. As the position of the slit changes, light scattered from different points on the sample become able to pass through the slit whilst light scattered from other points are blocked by the screen.

Figure 6:
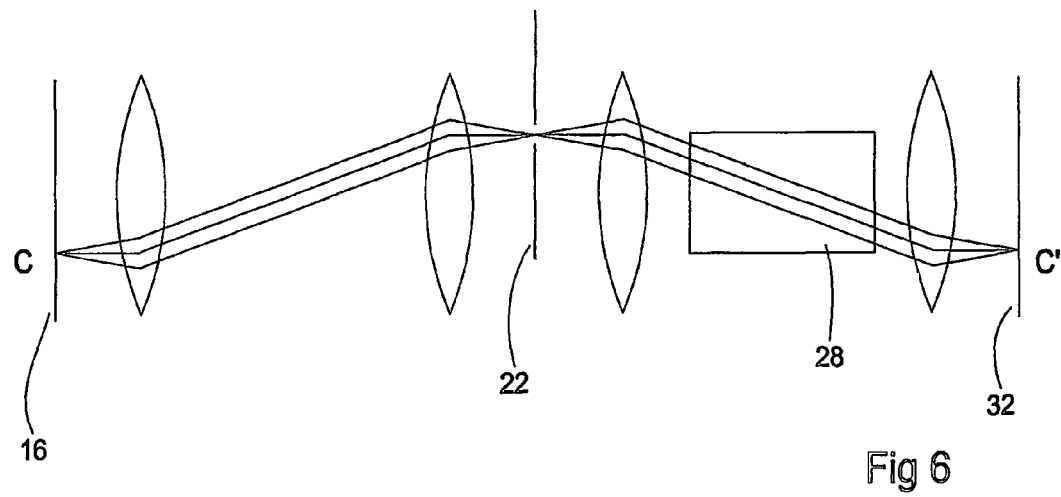
FIGS. 6 and 7 are schematic plan views of the first embodiment showing a movable slit.
Figure 7:
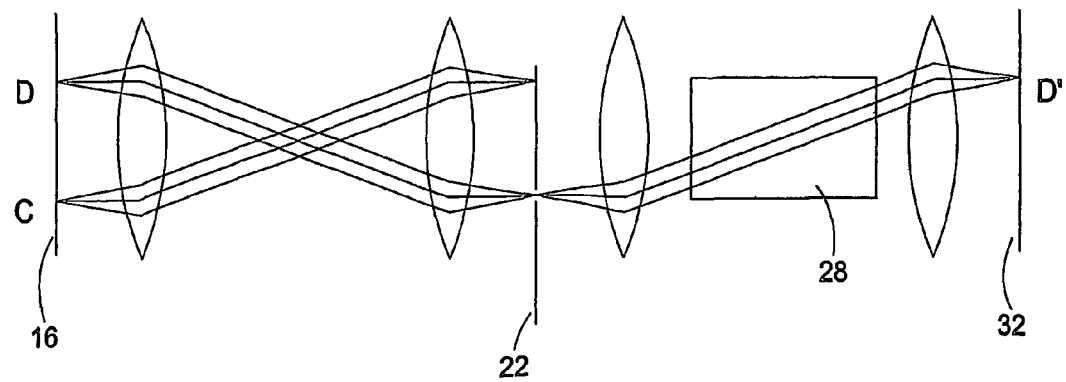

FIG. 6 shows the slit of the spatial filter in a first position. Light scattered from point C on the sample passes through the slit to be incident on the CCD at point C'. However when the slit is moved to a position shown in FIG. 7, the light scattered from point C is blocked by the screen, whilst light scattered from point D passes through the slit to be incident on the CCD at point D'.

It is normal for spectroscopic apparatus to be calibrated. In particular it is necessary to know the wavenumber k corresponding to each position in the x-direction across the detector (i.e. in the direction in which the spectrum is dispersed when the analyser 28 is a dispersive device such as a grating). This is known as X-axis calibration and disclosed in International Patent Application No. WO01/94897. However as the position of the slit is altered, an error in the X-axis calibration results and this should desirably be corrected. The computer controlling the movement of the slit and "virtual slit" should add an error adjustment for the X-axis calibration with respect to each position of the slit when analysing the data from the CCD.

Alternatively if the laser is defocused on the sample, the analysed light may be captured in a single exposure. In this case, the sample is scanned by moving the slit in a horizontal direction as described above. However the "virtual slit" is not moved in the vertical direction. Instead each row of pixels acts as a stationary "virtual slit", receiving light from a corresponding row on the sample.

Figure 8:
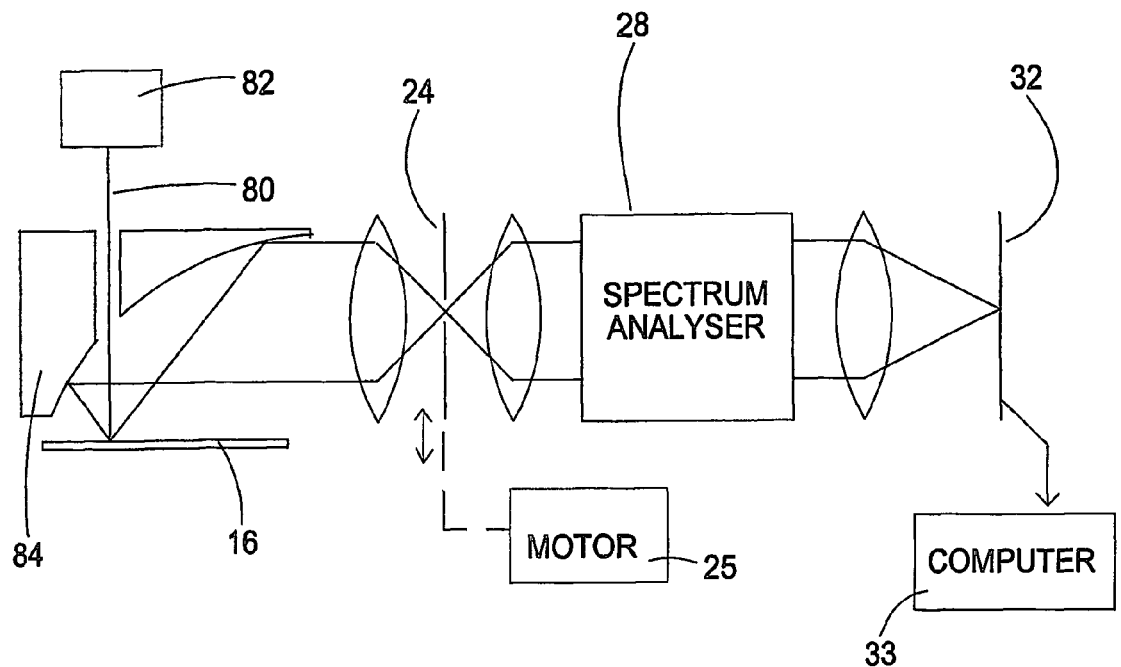
FIG. 8 is a schematic diagram of a second embodiment combining a scanning electron microscope with the spectroscopy apparatus.

In a second embodiment, the spectroscopy apparatus is combined with a scanning electron microscope (SEM) as in FIG. 8. Where the components of the spectroscopy apparatus are similar to those in FIG. 1, the same reference numerals have been used and need not be described further. An electron beam 80 from the scanning electron microscope 82 scans the sample, the irradiation of the sample by the electron beam causing cathodoluminescence. This emitted light is reflected by a parabolic mirror 84 into the spectroscopy apparatus. The movement of the slit in the spatial filter and the "virtual slit" of the CCD are controlled by the same computer as, and are timed to move synchronously with, the electron beam, resulting in a two-dimensional confocal map of the sample being produced in the photodetector. This has the advantage that the electron beam is focused at one point of the sample at a time, so there is no interference from adjacent points in the sample.

Figure 9:
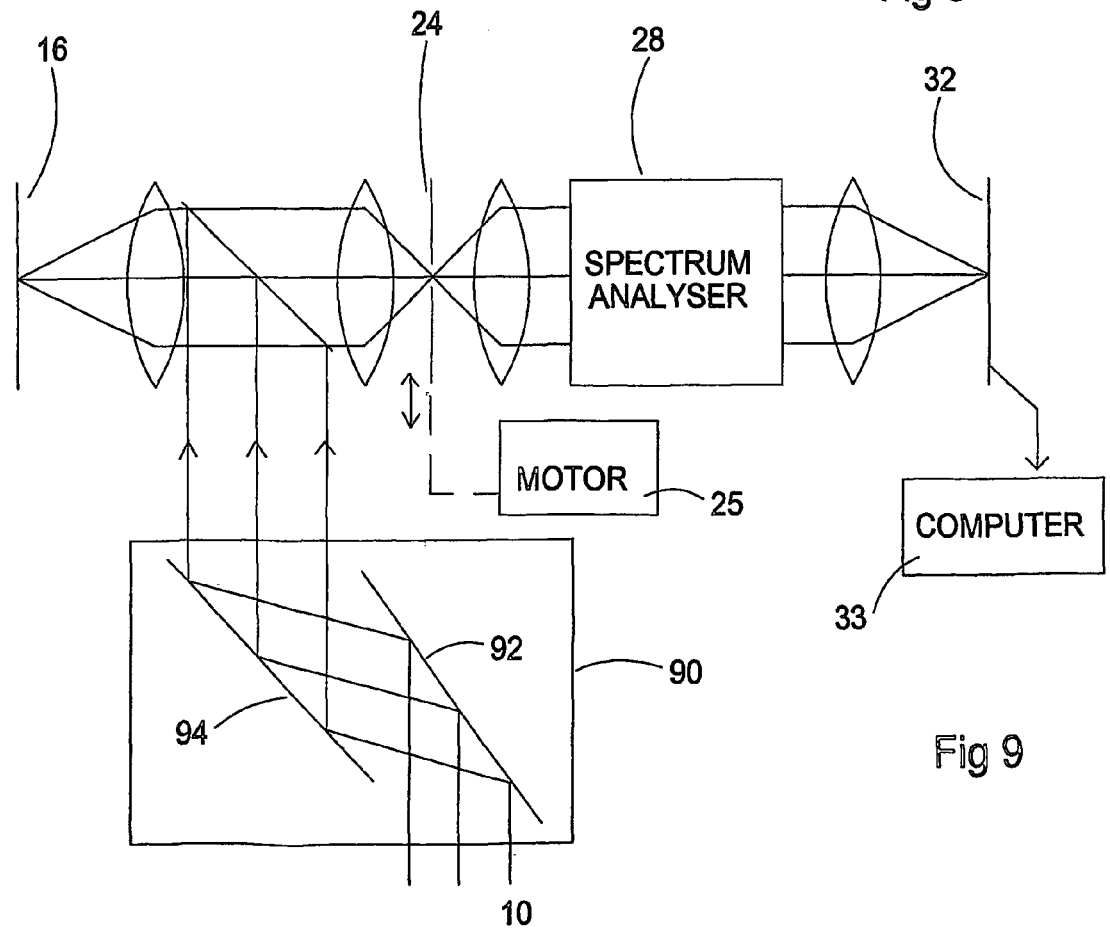
FIG. 9 is a schematic diagram of a third embodiment which uses a scanning laser.

FIG. 9 shows a third embodiment of the invention in which a scanning laser is used to illuminate the sample. This embodiment is identical to the embodiment shown in FIG. 1, with the exception that a beam steering unit 90 is added between the laser and the dichroic filter. The beam steering unit may comprise two mirrors 92 and 94, both independently tiltable about respective mutually orthogonal axes so that the focused laser beam may be scanned across the surface of the sample in a two-dimensional (x-y) raster scan. The slit on the spatial filter and the "virtual slit" of the CCD will move synchronously with the scanning laser beam, under the control of the same computer, as in the previous embodiment.

Figure 10:
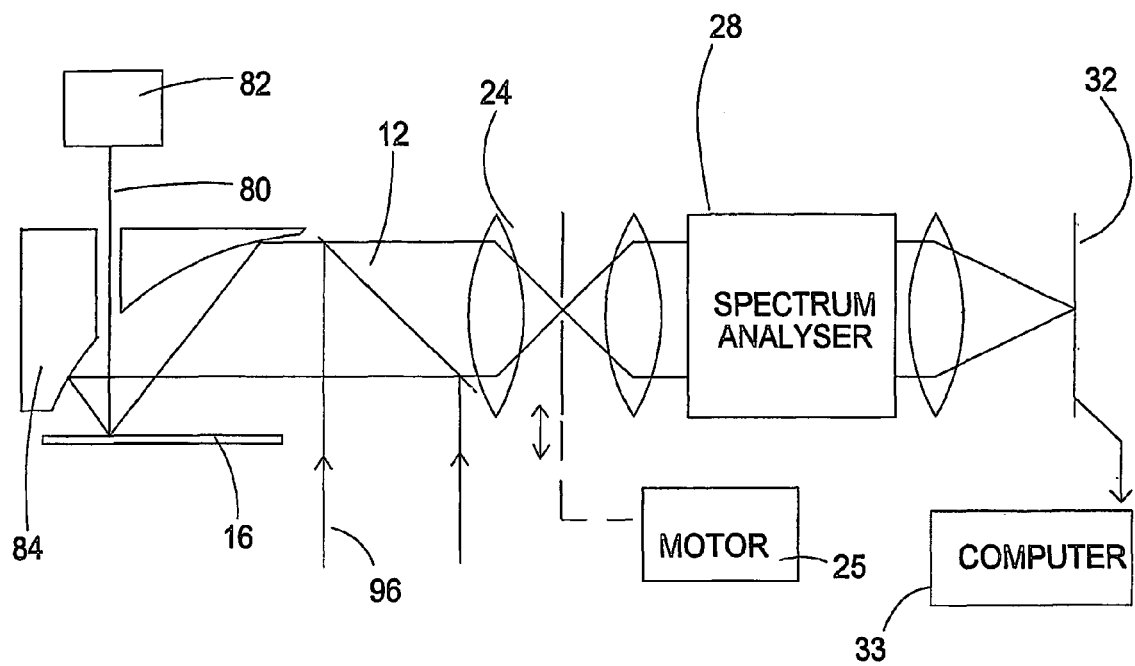
FIG. 10 is a schematic diagram of an embodiment of the invention comprising a combination of the second and third embodiments illustrated in FIGS. 8 and 9 respectively.

FIG. 10 shows an embodiment of the invention which is a combination of the apparatus shown in FIGS. 8 and 9. In this embodiment the sample may be scanned by the electron beam 80 from the scanning electron microscope 82 as described in the second embodiment or by light 96 from a scanning laser as described in the third embodiment.

Figure 11:
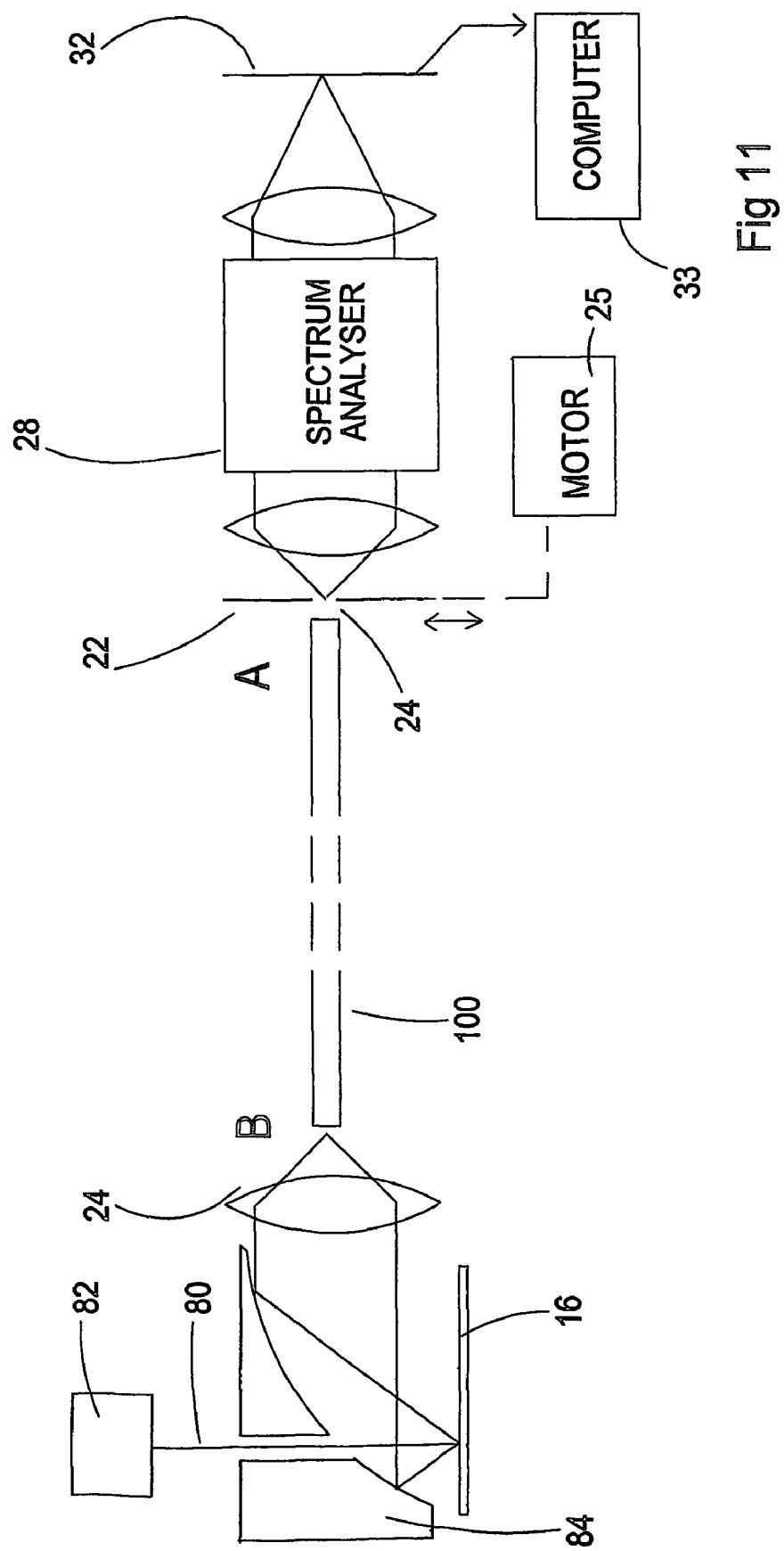
FIG. 11 is a schematic diagram of the embodiment illustrated in FIG. 8 in which the scanning electron microscope is remote from the spectroscopy apparatus.

It may be desired to separate the spectroscopy apparatus from the scanning electron microscope or sample and light source. FIG. 11 illustrates an arrangement in which the spectroscopy apparatus is remote from a scanning electron microscope and light is channeled from the sample to the spectroscopy apparatus through one or more optical fibres 100.

Figure 12:
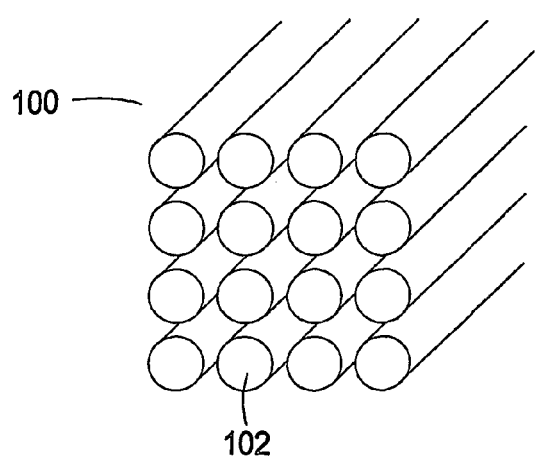
FIG. 12 is a schematic diagram of a two-dimensional array of optical fibres linking the scanning electron microscopy and spectroscopy apparatus.

The one or more optical fibres 100 may comprise a two dimensional array of optical fibres 102 as shown in FIG. 12. As described in previous embodiments, the sample is scanned in the y direction by movement of the virtual slit on the photodetector in the y direction and the sample is scanned in the x direction by moving the slit 22 in the x direction. The slit is located between the spectroscopy apparatus and the end A of the optical fibres 102 adjacent the spectroscopy apparatus. Alternatively the sample may be scanned in the x direction by keeping the slit 22 in a fixed position and moving the end A of the optical fibres 102 adjacent the spectroscopy apparatus in the x direction. Thus for every position of the virtual slit in the y direction the end A of the optical fibres 102 is scanned along the x direction. This method has the advantage that as the slit remains in a fixed position, there is no requirement to correct the X calibration for each position of the slit.

Hence the optical fibres 100 are fixed at the end B adjacent the SEM and may be either fixed or moveable at the end A adjacent the spectroscopy apparatus.

Although the description refers to Raman spectroscopy, the above methods are also suitable for other types of spectroscopy, for example fluorescence, cathodoluminescence and photoluminescence.

The invention claimed is:

1. A spectroscopy method, comprising:
   illuminating or irradiating a sample to obtain a spectrum of scattered light;
   analysing the spectrum;
   passing a plurality of components of the analysed spectrum to a photodetector, wherein light scattered from a given plane in the sample is brought to a tight focus in a given area on the photodetector and light scattered from other planes in the sample is brought to a more diffuse focus on the photodetector;
   wherein light received in said given area is detected without or separately from light outside the given area, thereby reducing the effect of light scattered from other planes in the sample;
   characterised in that the position of the given area on the photodetector in which light received is detected may be moved in order that light from a first point in a given plane of the sample is detected by the given area in a first position on the photodetector and light from a second point in the given plane of the sample is detected by the given area in a second position on the photodetector.

2. A spectroscopy method according to claim 1 in which the step of detecting light in said given area on the photodetector provides confocal action in one dimension.

3. A spectroscopy method according to claim 2 in which confocal action is provided in a second dimension by providing a confocal aperture through which the scattered light passes, comprising a screen with a slit positioned such that light from a given plane in the sample passes through the slit but light from other planes in the sample are blocked by the screen.

4. A spectroscopy method according to claim 1, wherein the scattered light is passed through a confocal aperture to reduce light from non-desired planes which is passed to the photodetector;
   and wherein the aperture is movable such that in a first position, light from a first point in the sample may pass through the aperture onto the photodetector, and in a second position light from a second point in the sample may pass through the aperture onto the detector.

5. A spectroscopy method according to claim 1 wherein the photodetector comprises a two-dimensional array of photodetector elements.

6. A spectroscopy method according to claim 4 in which the photodetector comprises an array of photodetector elements and wherein the wavenumber versus position on the array in a direction transverse to the slit may be calibrated for the initial position of the slit and a calibration correction performed for each subsequent position of the slit.

7. A spectroscopy method according to claim 3 wherein at least one optical fibre is provided between the sample and the confocal aperture for passage of scattered light from the sample to the confocal aperture.

8. A spectroscopy method according to claim 7 wherein the confocal aperture is stationary and wherein the end of the optical fibre adjacent the confocal aperture is movable such that in a first position, light from a first point on the sample may pass through the slit of the confocal aperture onto the photodetector and in a second position light from a second point in the sample may pass through the slit onto the photodetector.

9. A spectroscopy method according to claim 1 wherein a scanning electron microscope is used to irradiate the sample.

10. A spectroscopy method, comprising:
    illuminating or irradiating a sample to obtain a spectrum of scattered light;
    analysing the spectrum;
    passing a plurality of components of the analysed spectrum to a photodetector;
    wherein the scattered light is passed through a confocal aperture to reduce light from non-desired planes which is passed to the photodetector;
    and wherein the aperture is movable such that in a first position, light from a first point in the sample may pass through the aperture onto the photodetector, and in a second position light from a second point in the sample may pass through the aperture onto the detector.

11. A spectroscopy method according to claim 10 wherein the confocal aperture comprises a screen with a slit.

12. A spectroscopy method according to claim 10 in which the photodetector comprises an array of photodetector elements and wherein the wavenumber versus position on the array may be calibrated for the initial position of the aperture and a calibration correction performed for each subsequent position of the aperture.

13. A spectroscopy method according to claim 10 wherein at least one optical fibre is provided between the sample and the confocal aperture for passage of scattered light from the sample to the confocal aperture.

14. A spectroscopy apparatus, comprising:
illuminating or irradiating means for illuminating or irradiating a sample to obtain a spectrum of scattered light;
analysing means for analysing the spectrum;
a photodetector for detecting a plurality of components of the analysed spectrum, wherein light scattered from a given plane in the sample is brought to a tight focus in a given area on the photodetector and light scattered from other planes in the sample is brought to a more diffuse focus on the photodetector;
selection means, which enables light received in said given area to be detected without or separately from light outside the given area, thereby reducing the effect of light scattered from other planes in the sample;
characterised in that the selection means may move the area on the photodetector in which light received is detected in order that light from a first point in a given plane of the sample is detected by the given area in a first position on the photodetector and light from a second point in the given plane of the sample is detected by the given area in a second position on the photodetector.

15. A spectroscopy apparatus according to claim 14 wherein the selection means which enables light to be detected in said given area on the photodetector provides confocal action in one dimension.

16. A spectroscopy apparatus according to claim 15 in which confocal action is provided in a second dimension by a confocal aperture through which the scattered light passes, comprising a screen with a slit positioned such that light from a given plane in the sample passes through the slit but light from other planes in the sample are blocked by the screen.

17. A spectroscopy apparatus according to claim 14 wherein the scattered light is passed through a confocal aperture to reduce light from non-desired planes which is passed to the photodetector;
and wherein the aperture is movable such that in a first position, light from a first point in the sample may pass through the aperture onto the photodetector, and in a second position light from a second point in the sample may pass through the aperture onto the detector.

18. A spectroscopy apparatus according to claim 14 wherein the photodetector comprises a two-dimensional array of photodetector elements.

19. A spectroscopy apparatus according to claim 17 wherein the photodetector comprises an array of photodetector elements and wherein calibration means are provided to calibrate the wavenumber versus position on the array in a direction transverse to the slit from the initial position of the slit and to perform a calibration correction for each subsequent position of the slit.

20. A spectroscopy apparatus according to claim 16 wherein at least one optical fibre is provided between the sample and the confocal aperture for passage of scattered light from the sample to the confocal aperture.

21. A spectroscopy apparatus according to claim 20 wherein the confocal aperture is stationary and wherein the end of the optical fibre adjacent the confocal aperture is movable such that in a first position, light from a first point on the sample may pass through the slit of the confocal aperture onto the photodetector and in a second position light from a second point in the sample may pass through the slit onto the photodetector.

22. A spectroscopy apparatus according to claim 14 wherein the irradiating means comprises a scanning electron microscope.

23. A spectroscopy apparatus, comprising:
illuminating or irradiating means for illuminating or irradiating a sample to obtain a spectrum of scattered light;
analysing means for analysing the spectrum;
a photodetector for detecting a plurality of components of the analysed spectrum;
a confocal aperture, said scattered light being passed through the confocal aperture to reduce light from non-desired planes which is passed to the photodetector;
wherein the confocal aperture is movable such that in a first position, light from a first point in the sample may pass through the aperture onto the photodetector, and in a second position light from a second point in the sample may pass through the aperture onto the detector.

24. A spectroscopy apparatus according to claim 23 wherein the confocal aperture comprises a screen with a slit.

25. A spectroscopy apparatus according to claim 23 in which the photodetector comprises an array of photodetector elements and wherein calibration means are provided to calibrate the wavenumber versus position on the array for the initial position of the aperture and to correct the calibration for each subsequent position of the aperture.

26. A spectroscopy apparatus according to claim 23 wherein at least one optical fibre is provided between the sample and the confocal aperture for passage of scattered light from the sample to the confocal aperture.

* * * * *